US 6,666,100 B1

(12) United States Patent
Snyder

(10) Patent No.: US 6,666,100 B1
(45) Date of Patent: Dec. 23, 2003

(54) SAMPLE INJECTOR WITH INTERFACE-CONTROL LEVER

(75) Inventor: Philip A. Snyder, Ann Arbor, MI (US)

(73) Assignee: Merlin Instrument Company, Half Moon Bay, CA (US)

( * ) Notice: Subject to any disclaimer, the term of this patent is extended or adjusted under 35 U.S.C. 154(b) by 0 days.

(21) Appl. No.: 10/319,996

(22) Filed: Dec. 16, 2002

(51) Int. Cl.$^7$ .............................................. G01N 01/00
(52) U.S. Cl. ................................................. 73/864.87
(58) Field of Search ....................... 73/864.21, 864.87, 73/864.83, 864.23, 864.25; 604/218

(56) References Cited

U.S. PATENT DOCUMENTS

| | | | |
|---|---|---|---|
| 3,880,163 A | * 4/1975 | Ritterskamp | 604/136 |
| 4,711,250 A | * 12/1987 | Gilbaugh et al. | 600/578 |
| 4,838,869 A | * 6/1989 | Allard | 604/195 |
| 4,959,056 A | * 9/1990 | Dombrowski et al. | 604/186 |
| 4,966,593 A | * 10/1990 | Lennox | 604/198 |
| 5,026,349 A | * 6/1991 | Schmitz et al. | 604/134 |
| 5,686,656 A | * 11/1997 | Amirav et al. | 73/23.41 |
| 5,756,905 A | * 5/1998 | Ueda | 73/864.24 |
| 6,257,076 B1 | 7/2001 | Snyder et al. | 73/864.87 |

FOREIGN PATENT DOCUMENTS

EP          0108529 A1  *  5/1984 ............ A61M/5/20

* cited by examiner

Primary Examiner—Daniel S. Larkin
Assistant Examiner—Katina Wilson
(74) Attorney, Agent, or Firm—Clifton L. Anderson

(57) ABSTRACT

A manual sample injector includes a syringe holder, a plunger driver, and an interface. An interface-control lever attached to the interface can assume "extraction", "injection", and "safety" orientations. In its safety orientation, the interface-control lever maintains a syringe needle in a retracted position for safety. Mounting the sample injector on a sample vial forces the interface-control lever to its extraction orientation, which allows the syringe needle to extend into the sample vial for sample extraction. The extent of the needle into the sample vial can be adjusted for precise extraction of sample from non-uniform vial contents. Mounting the injector on an injection port forces the interface-control lever to its injection orientation so that the syringe needle can be extended to an appropriate depth for sample injection. The actual injection is motivated by a plunger-driver spring that urges the plunger driver toward the syringe holder when a release lever is actuated.

10 Claims, 14 Drawing Sheets

SAMPLE INJECTOR WITH INTERFACE-CONTROL LEVER

BACKGROUND OF THE INVENTION

The present invention relates to chemical analysis and, more particularly, to devices for injecting samples into analytical equipment. A major objective of the present invention is to provide for improved manual injection of a sample into a gas chromatography (GC) system.

The contributions of the medical, environmental and life sciences to humanity have been facilitated by advances in chemical analysis. Many analytical techniques provide for the division of a complex sample into its components. Gas chromatography is one such analytical technique that separates volatized chemical components according to their relative partitioning between a gaseous mobile phase and a stationary (typically solid) phase. The solid phase is bound within a chromatography column, through which the mobile phase flows. In general, greater separation can be achieved using narrower-bore columns, with capillary separation columns being state of the art.

Especially with capillary columns, the volume and rate of sample introduced are critical. These parameters are best addressed in the context of automated systems. These can inject a sample soon after a needle penetrates an injection septum, and they can inject with high velocities in a repeatable manner. However, an autoinjector may be unavailable for reasons of cost, portability, downtime, and unsuitability for a given task. In these circumstances, manual injection is an attractive and sometimes necessary alternative. However, human physical control tends to be rather gross and slow relative to the demands of capillary GC sample injection. U.S. Pat. No. 6,257,076 to Snyder et al., incorporated by reference in its entirety herein, discloses a manual sample injector that addresses the challenges of precise control over the volume and velocity of injected sample.

There remains a problem, however, regarding the precision with which a sample can be extracted, e.g., from a sample vial into a syringe. For example, if the sample is shallow within a vial, the tip of a syringe needle must be positioned precisely near the base of the vial. In another case, there might be precipitate at the base of the vial that is to be excluded from the sample to be injected into the chromatograph. For another example, it might be desired to extract sample from above or below an interface between two immiscible liquids and avoid the interface itself. Accordingly, what is needed is a manual sample injector that allows precise selection of the location within a vial from which sample is extracted. Furthermore, it is desirable to have this additional control while maintaining the ease of operation associated with the sample injector disclosed in above-referenced U.S. Patent.

SUMMARY OF THE INVENTION

The present invention provides a sample injector with an interface-control lever with "injection", "extraction" and, preferably, "safety" orientations. The interface-control lever orientation determines the limits of relative motion between a syringe holder (and thus a syringe needle) and an interface (and thus a sample vial or an injection port). When the interface-control lever is in the injection orientation, the syringe holder can move to a relative position in which the needle is maximally extended through the interface for injecting a sample into an injection port. When the interface-control lever is its extraction orientation, the syringe holder can move to an extraction position in which the needle extends an intermediate amount from the interface; this intermediate amount is suited for extracting sample from a sample vial and is preferably adjustable. When the interface-control lever is in its safety orientation, the syringe needle is prevented from extending out of the interface, reducing the likelihood of injury to a careless user.

The sample injector includes a plunger driver that grips a syringe plunger, which is used to control sample flow into and out of the syringe. Springs can be used to set default conditions for the interface-control lever, the sample holder, and the plunger driver. An interface-control-lever spring urges the interface-control lever toward its safety orientation. An interface spring urges the syringe holder away from the interface so that the syringe needle is retracted by default. A plunger-driver spring urges the plunger driver toward the sample holder so as to urge the syringe plunger toward its fully inserted position. This spring provides the actual force for sample injection, ensuring a precisely repeatable injection velocity.

The sample injector includes a release lever or other mechanism having cocked and release conditions. When the release is in its release condition, the plunger-driver spring forces the plunger driver to fully insert the plunger. When the release is in its cocked condition, the plunger driver is stopped at a position at which the amount of sample in the syringe is optimized for injection. When from this cocked condition, the release is moved to its release condition, the predetermined amount of sample in the syringe can be injected into an injection port at a predetermined rate by the action of the plunger-driver spring.

Movement of the release from its cocked position to its released position is forced by actuator attached to the interface. As the actuator is moved toward the release, the plunger-driver spring is loaded (deformed so that it applies an increased counterforce). Once the release has been moved past its released position by the actuator, the plunger driver motion is no longer limited by the release. The spring then urges the syringe holder toward the plunger driver. This forces the plunger fully into the syringe so that sample is injected.

The interface assembly ensures alignment of the syringe needle with sample vials (for extraction) and injection septa (for injection). During extraction and injection, the interface assembly typically has a fixed position relative to the injection port or vial. The interface-control lever is configured relative to the interface so that mounting the interface onto a sample vial causes the sample vial to contact the interface-control lever and move it to its extraction orientation. Likewise, the interface-control lever is configured so that mounting the interface onto an injection port (e.g., the septum nut), the injection port contacts the interface-control lever so as to move it to its injection orientation. Thus, the interface-control lever assumes an appropriate orientation automatically.

The sample injector also includes a catch that engages and holds a stop arm of the interface-control lever when the sample injector reaches its extraction condition (with the interface-control lever in its extraction orientation). When the stop arm is so caught, the interface spring cannot force the interface and the sample holder apart so that the needle is fixed in an extended position. This position determines the level of the needle tip within the vial, and thus the vial location from which sample is to be extracted. The catch can be attached to the sample holder and is preferably adjustable so that the extraction position, and thus the vial location from which sample is extracted, can be selected.

The precise control of syringe extent during sample extraction is a major advantage, especially when dealing with non-uniform samples. In addition, the invention allows convenient selection of safety, injection, and extraction modes. Furthermore, the use of the plunger-driver spring for sample injection ensures that an optimal injection velocity can be obtained injection after injection. These and other features and advantages of the invention are detailed below with reference to the following drawings.

In some figures, some components are omitted for clarity.

DETAILED DESCRIPTION

Figure 1:
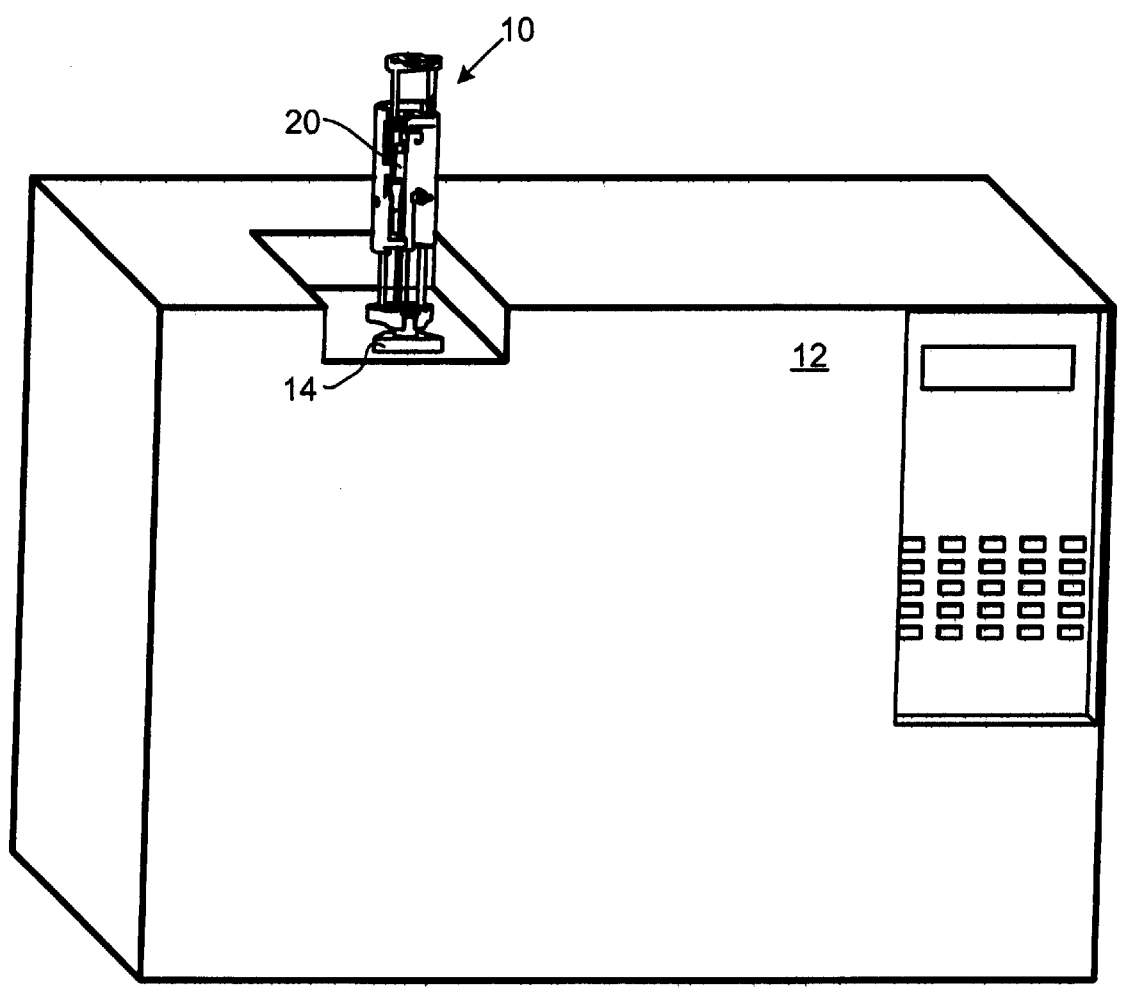
FIG. 1 is a schematic perspective illustration of a manual sample injector in accordance with the present invention in a preinjection condition on a gas chromatograph just prior to sample injection.
Figure 2:
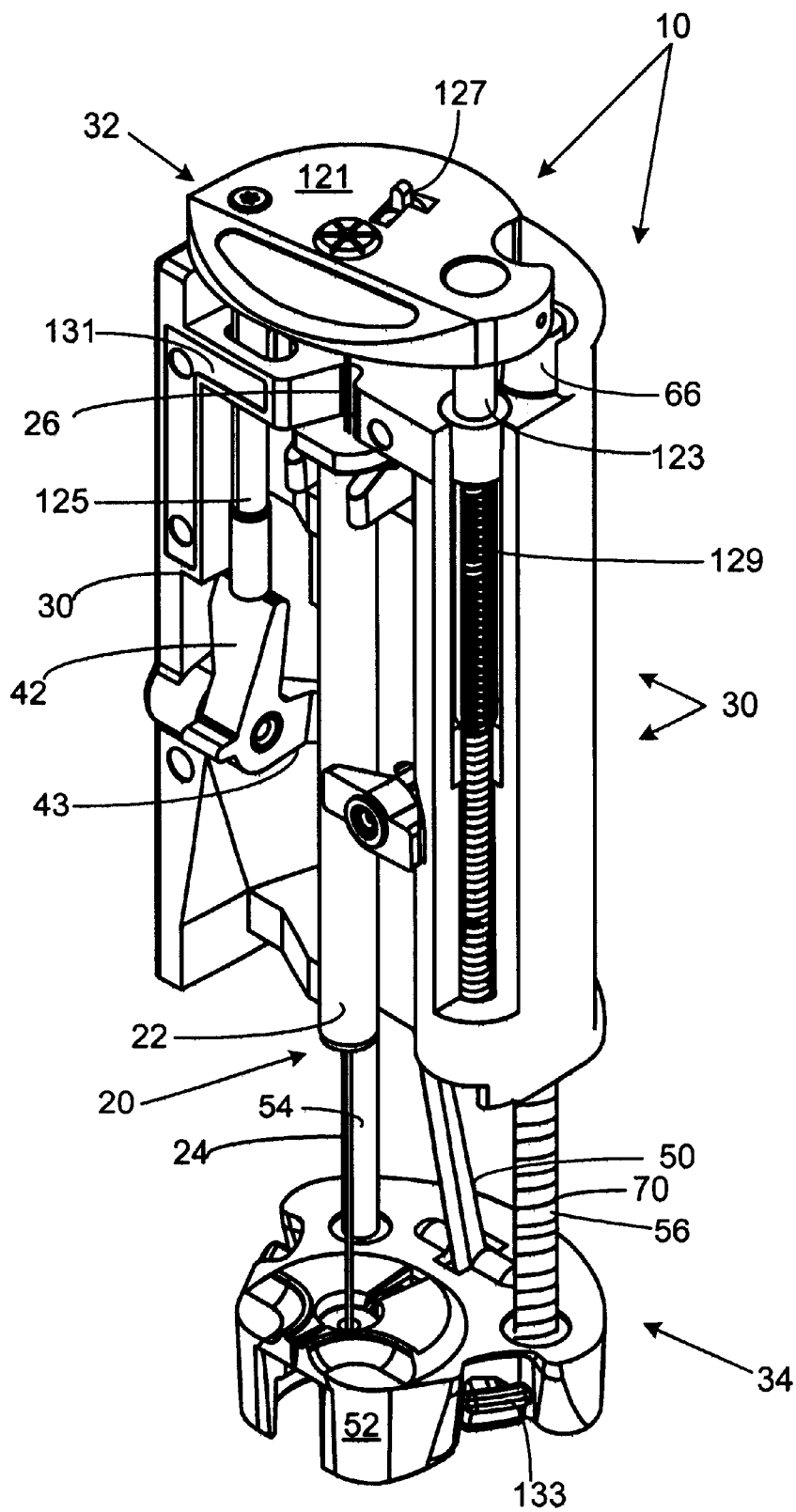
FIG. 2 is a perspective view of the manual sample injector of FIG. 1 in its cocked condition prior to mounting on an injection port with a cutaway showing the location of a plunger-driver spring.

A manual sample injector 10 in accordance with the present invention is designed for manual injection of a sample into a gas chromatograph 12 via the latter's injection port 14, as shown in FIG. 1. The sample is loaded into and injected from a syringe 20, which includes a syringe chamber 22, a syringe needle 24, and a plunger 26, as seen in FIG. 2. Sample injector 10 includes a syringe holder 30 for holding syringe chamber 22, a plunger driver 32 for operating syringe plunger 26, and an injection-port interface 34 for aligning syringe needle 24 with injection port 14 for injection or a sample vial 36 (shown in FIG. 3) for sample extraction. To these ends, syringe holder 30 is slideable relative to interface 34 in the dimension of the needle extent, and plunger driver 32 is slideable relative to syringe holder 30 in the same spatial dimension.

Figure 3:
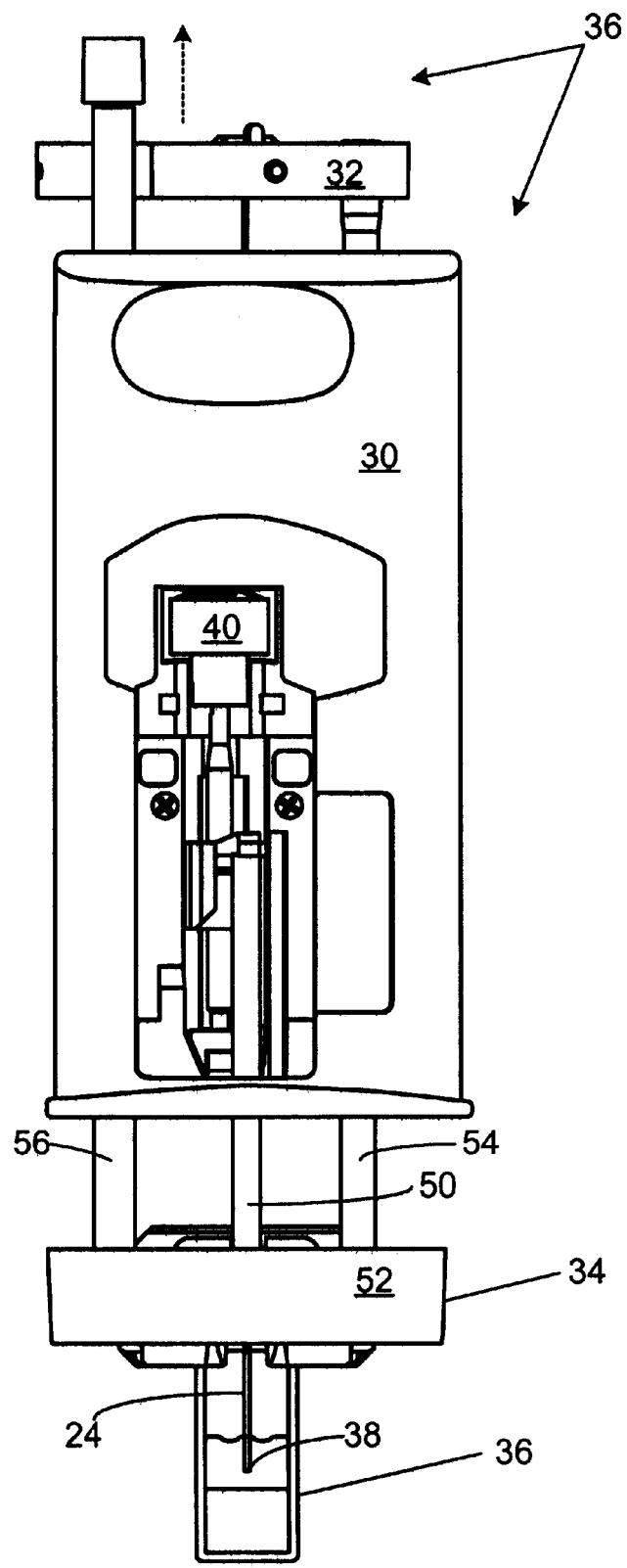
FIG. 3 is a rear-elevational view of the manual sample injector of FIG. 1 in its "pre-extraction" condition with the tip of a syringe needle above the interface between two liquids within a sample vial. A dotted arrow shows the direction a plunger-driver is moved to extract sample into syringe.
Figure 4:
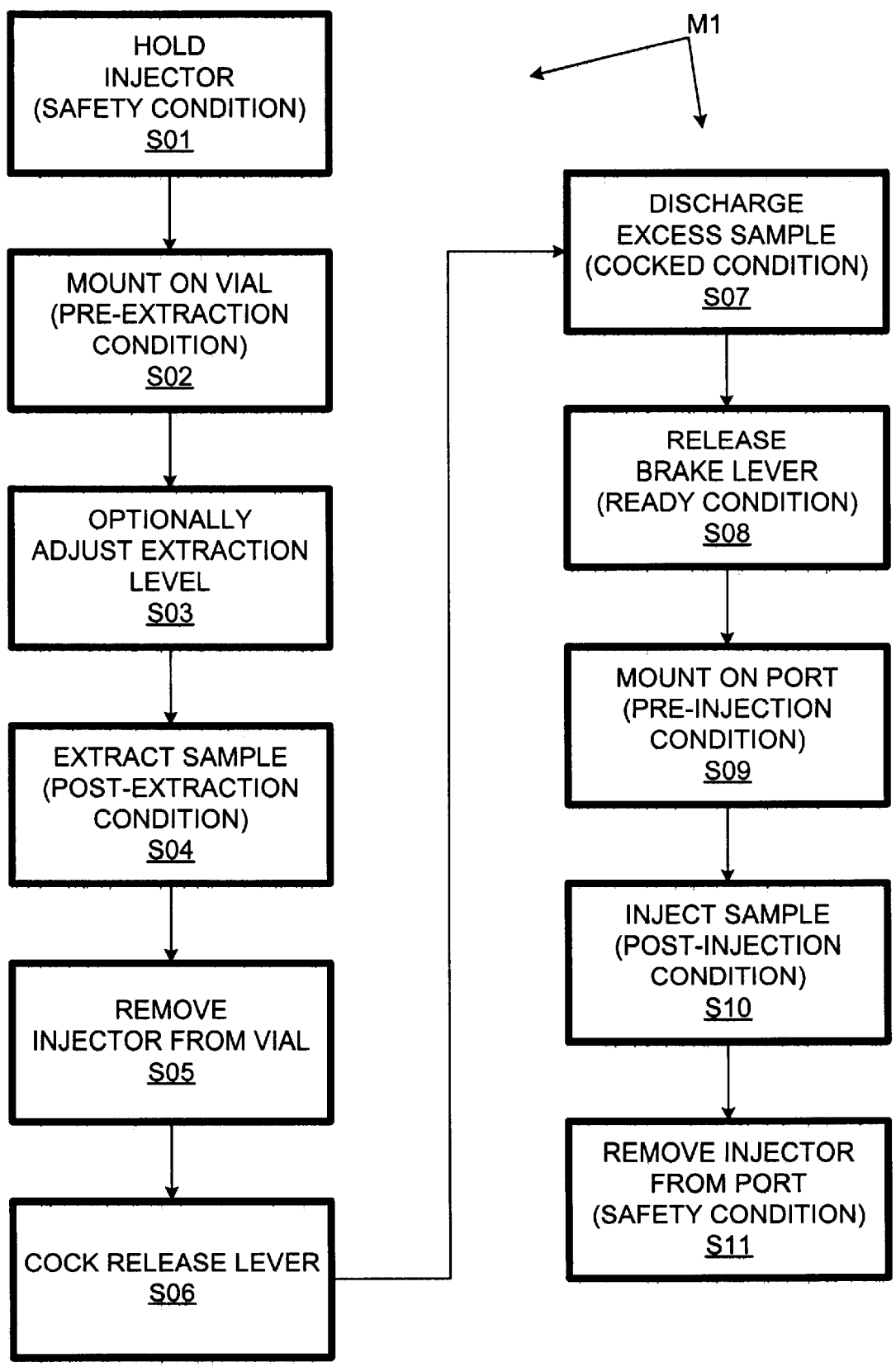
FIG. 4 is a flow chart of a method of using the manual sample injector of FIG. 1 from a user's perspective.

A method M1 of using sample injector 10 is flow-charted in FIG. 4. Initially, syringe needle 24 is fully retracted into interface 34 for safety. At a step S01, the user holds sample injector 10 by gripping syringe holder 30. At step S02, the user mounts sample injector 10 onto sample vial 36 (FIG. 3) so that syringe needle 24 extends into vial 36. At optional step S03, the level of a tip 38 of needle 24 within vial 36 can be adjusted by turning a thumbwheel 40 (FIG. 3) on the back of syringe holder 30. At step S04, sample is extracted from the vial 36 in excess by lifting plunger driver 32. At step S05, sample injector 10 is removed from sample vial 36.

At step S06, a release lever 42 (FIG. 2) is cocked. At step S07, excess sample is discharged from syringe chamber 22 by a spring pushing plunger-driver 32 toward syringe holder 30. Cocked release lever 42 stops the plunger-driver motion when only the desired sample volume remains in syringe chamber 22. At step S08, an interface-control lever 50 is then released so that syringe needle 24 retracts.

At step S09, the user mounts sample injector 10 on injection port 14 (FIG. 1). At step S10, the user injects the sample by pushing syringe holder 30 toward port interface 34 (FIG. 2). At step S11, the user removes sample injector 10 from injection port 14. Steps S10 and S11 can proceed in rapid succession as a user makes a motion much like that used to attach sheets of paper together using a stapler.

Figure 5:
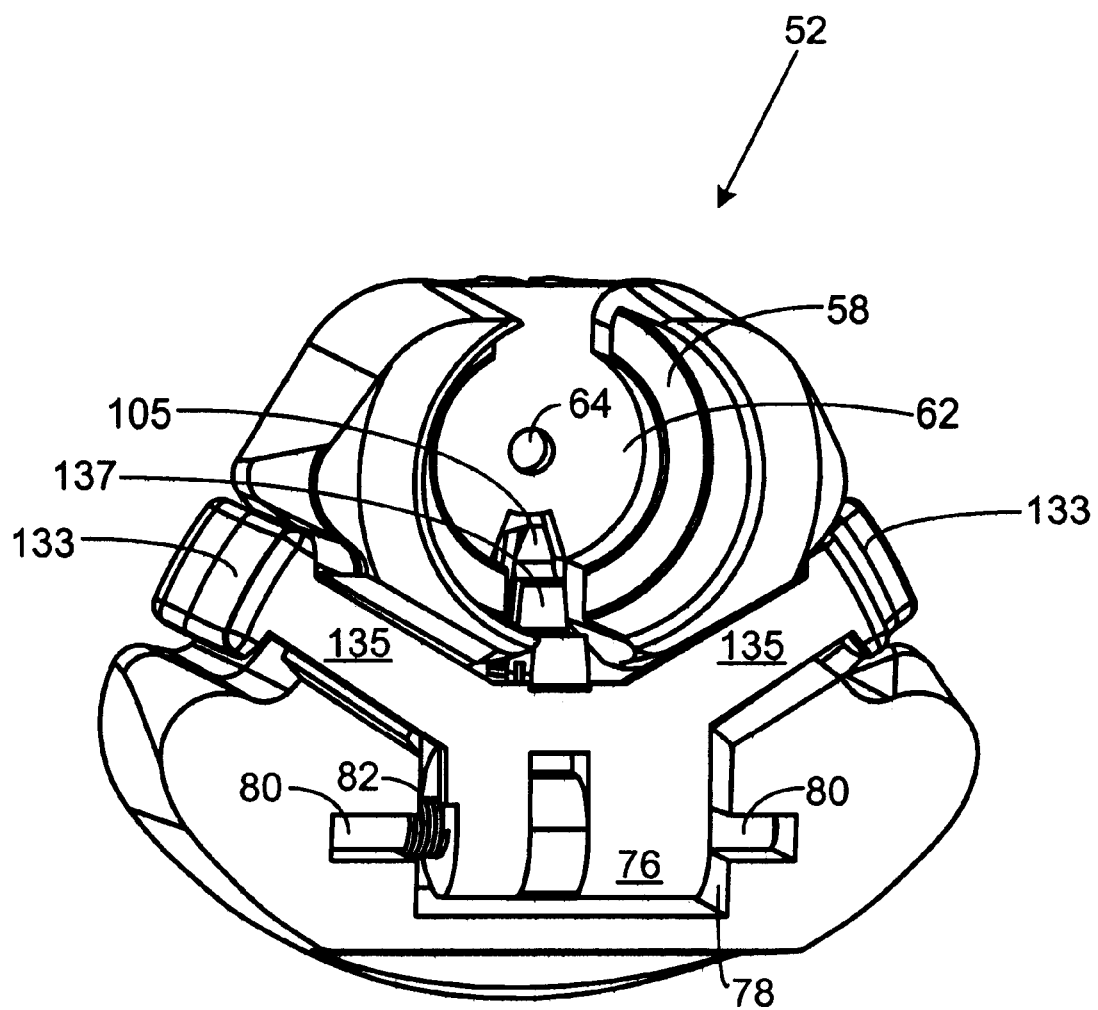
FIG. 5 is a bottom perspective view of an interface assembly of the sample injector of FIG. 1.

Port interface 34 includes a base 52, an actuator rod 54, and an interface guide rod 56, as shown in FIGS. 2 and 3. Base 52 is formed of Amodel resin; alternatively, another polysulfone or another high-temperature-resistant material can be used. Two concentric recessions are formed in the bottom of base 52, as shown in FIG. 5. An outer "injection" recession 58 is dimensioned to engage an injection-port septum nut. Injection recession 58 is slightly beveled so that a septum nut 60 (FIG. 12) of injection port 14 is readily "captured" and then guided to a snug fully engaged position. A smaller diameter inner "extraction" recession 62 is formed in the base of injection recession 58. Extraction recession 62 is dimensioned to engage the top of sample vial 36. A needle-extension aperture 64 extends through the base of extraction recession 62.

Interface guide rod 56 is attached to base 52 at one end, and is fitted with a rubber guide cap 66 at the other, as shown in FIG. 2. Guide cap 66 marks a limit to the relative distance syringe holder 30 can be moved from interface base 52; the limiting mechanism is an E-clip attached to a groove in interface guide rod. When the relative movement reaches this limit, syringe needle 24 is fully retracted into interface base 52 as illustrated in FIG. 2. An interface guide spring 70 is coiled about guide rod 56 so as to urge syringe holder 30 and interface base 52 apart so that syringe needle 24 is retracted.

Figure 6:
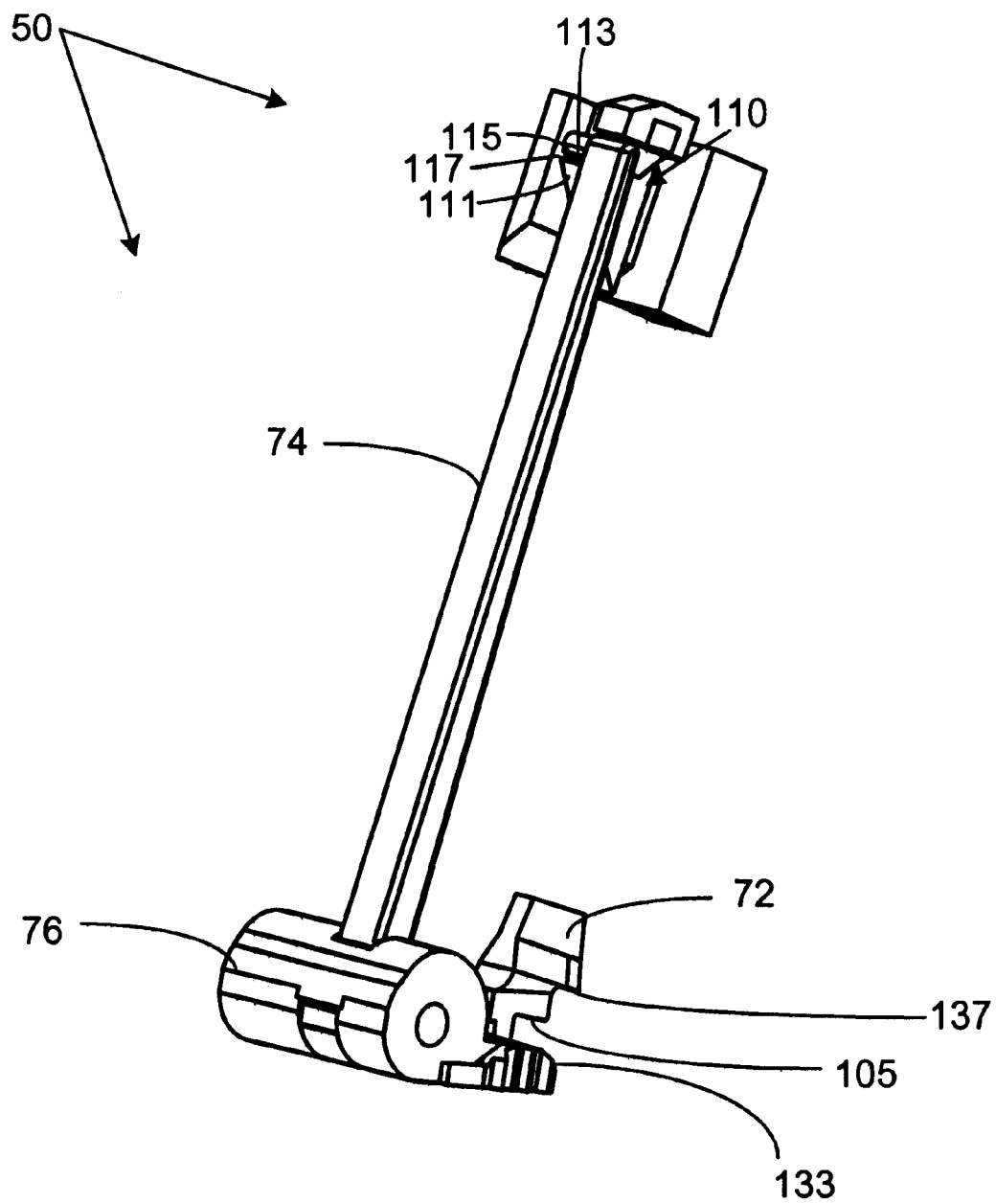
FIG. 6 is a perspective view of an interface-control lever of the interface assembly of FIG. 5 along with a catch of the syringe holder.

Interface-control lever 50 is pivotably attached to interface 34. Interface-control lever 50 includes a "control" arm 72, a "stop" arm 74, and a fulcrum 76, as shown in FIG. 6. Fulcrum 76 is seated in a rectangular recession 78 on the bottom of interface base 52, as shown in FIG. 5. An interface-control lever pivot rod 80, extends longitudinally along rectangular recession 78, defining a rotational axis for interface-control lever 50. An interface-control-lever spring 82 is attached at one end to fulcrum 76 and is coiled around pivot rod 80.

Figure 7:
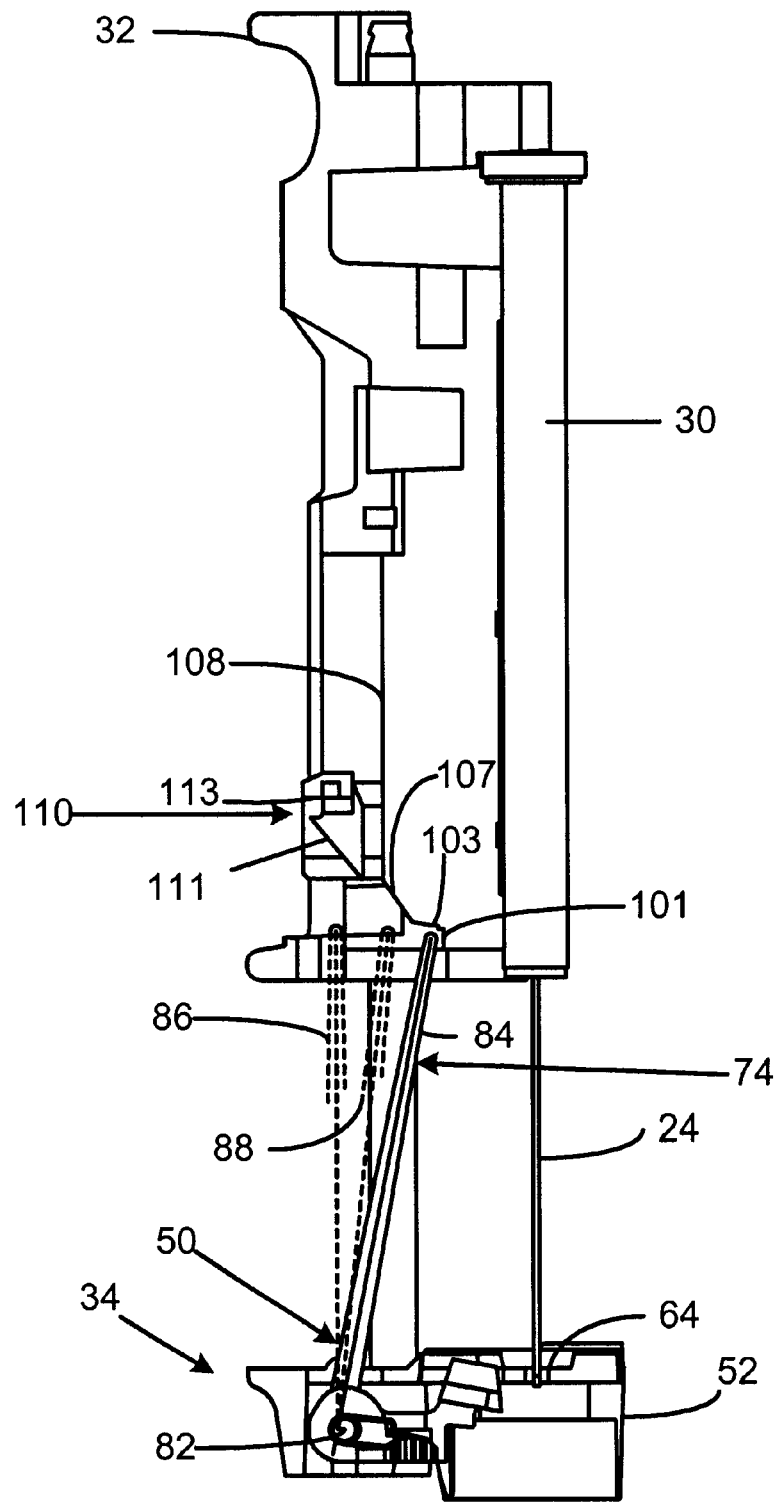
FIG. 7 is an elevational view of the manual sample injector of FIG. 1 in its safety condition (but showing extraction and injection orientations in dash).

Interface-control lever 50 can assume "safety", "extraction", and "injection" orientations (indicated, respectively, at 84, 86, and 88) as shown in FIG. 7. Interface-control-lever spring 82 urges interface-control lever 50 toward its "safety" orientation 84. More specifically, if sample injector 10 is in its fully retracted condition and there is no counter force, spring 82 forces interface-control lever 50 to its safety orientation 84, in which case, sample injector 10 assumes its safety condition, as shown in FIG. 7. This safety condition is assumed at the beginning (step S01) and end (step 10) of method M1. Further rotation is prevented by a portion 101 of syringe holder 30 that contacts stop arm 74 when interface-control lever 50 is in its safety orientation.

When sample injector 10 is in its safety condition, a distal end of stop arm 74 sits near a ledge 103 formed in syringe holder 30. In this case, when force is applied to move syringe holder 30 toward interface base 52, stop arm 74 contacts ledge 103, preventing further approach. This travel limit prevents syringe needle 24 from extending all the way through needle aperture 64, protecting the needle as well as the user from unintended contact.

Figure 8:
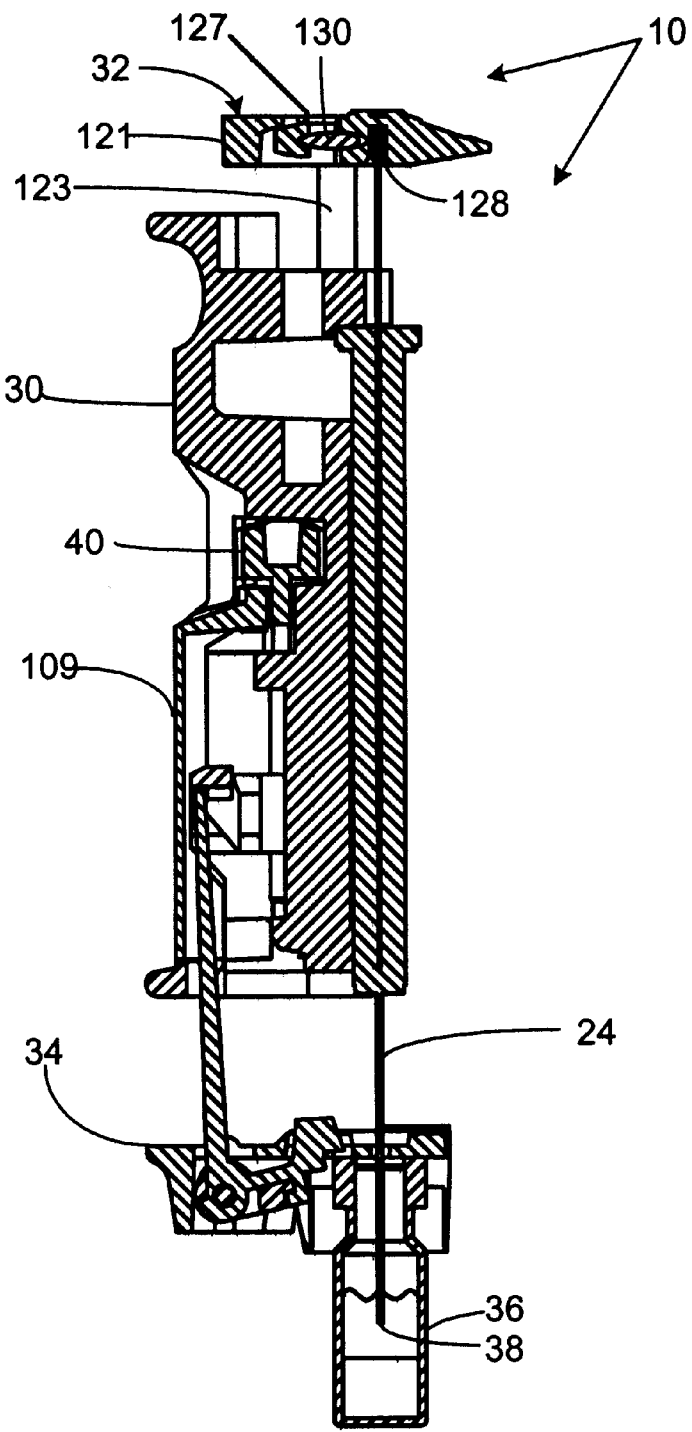
FIG. 8 is a schematic side view showing the injector of FIG. 1 in its post-extraction condition and mounted on the sample vial of FIG. 7.

Step S02 of FIG. 3, involves mounting sample injector 10 onto sample vial 36 so that it assumes a pre-extraction condition as shown in FIG. 8. Extraction recession 62 (FIG. 5) mates with the top of the sample vial 36. As it enters extraction recession 62 (FIG. 5), the sample vial top contacts an "extraction" ledge 105 (FIG. 5) of control arm 72 (FIG. 6) of interface-control lever 50 that extends into extraction recession 62. When the sample vial top is completely inserted into extraction recession 62, extraction ledge 105 is depressed to an extent that interface-control lever 50 assumes its extraction orientation 86 against a back wall 109 of syringe holder 30.

When interface-control lever 50 is in its extraction orientation 86, the relative motion of syringe holder 30 and interface 34 is no longer constrained by safety ledge 103. Instead, stop arm 74 is free to move up toward catch 110. Thus, the user can (e.g., at step S02) hold syringe holder 30 and force it down toward interface 34 so that stop arm 74 slides up within syringe holder 30.

As the downward motion of syringe holder 30 continues, the distal end of stop arm 74 contacts a catch 110. Catch 110 has an angled bottom 111 that forces the distal end of stop arm 74 toward 20 back wall 109 (FIG. 8) until angled bottom 111 is cleared. After another millimeter of motion, stop arm 74 contacts an upper ledge 113 of catch 110, which serves as a relative motion limit. If the downward pressure on syringe holder 30 is relaxed, a horizontal finger 115 at the distal end of stop arm 74 catches in a slot 117 between angled bottom 111 of catch 110 and upper edge 113 of catch 110.

At this point, the manual pressure on syringe holder 30 can be released. Since finger 115 is trapped in slot 117, an intermediate "extraction" position of syringe holder 30 relative to interface 34 is maintained. While there may be some play (on the order of a millimeter) in the position of catch 110, interface guide rod spring 70 forces syringe holder 30 away from inter face 34 to a limit of the play in the catch position so that the needle extent is precisely repeatable. This is the pre-extraction condition shown in FIG. 8 for sample injector 10.

The catch position is selected so that syringe needle 24 extends a predetermined distance into sample vial 36. Presumably, this distance is suitable for extracting the desired sample from vial 36. However, if the level of needle tip 38 in vial 36 is not the desired one, at optional step S03, the catch position can be adjusted by turning thumb wheel 40 on the back of syringe holder 30. Thumb wheel 40 drives a screw to which catch 110 is attached so as to change its vertical position (and thus the position of needle tip 38 in vial 36). This feature is particularly useful where sample is to be drawn from a non-uniform composition; for example, where sample is to be drawn from one of two immiscible liquids, as indicated in FIG. 8.

Once syringe needle tip 38 is at the desired elevation within sample vial 36, sample can be extracted by lifting plunger driver 32 (relative to syringe holder 30) at step S04 (FIG. 2). Once an excess amount of sample has been extracted, sample injector 10 assumes its 25 post-extraction condition as shown in FIG. 8.

Figure 9:
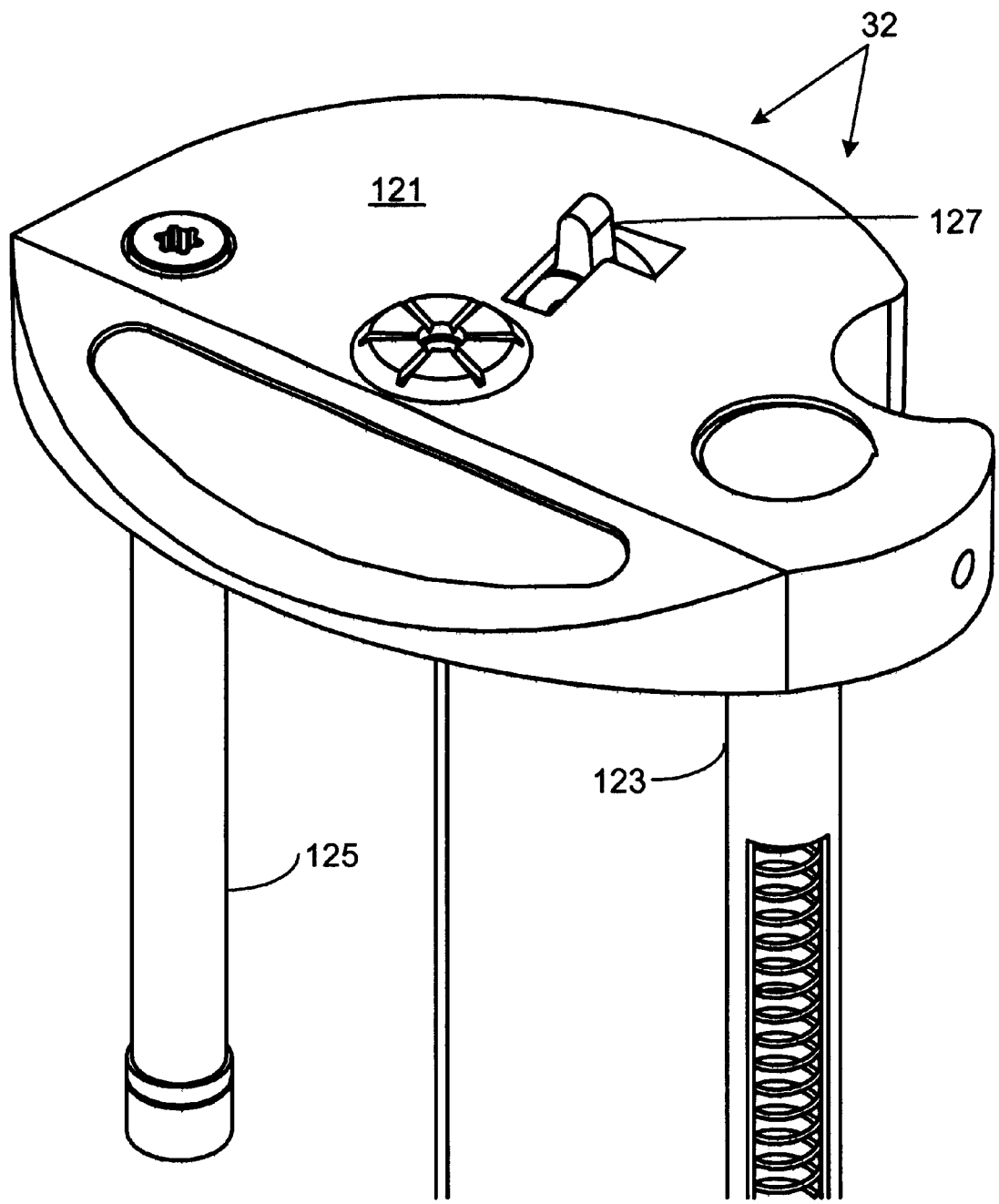
FIG. 9 is a perspective view of the plunger driver of FIG. 7 with a plunger-driver spring coiled around a plunger-driver guide rod.
Figure 10:
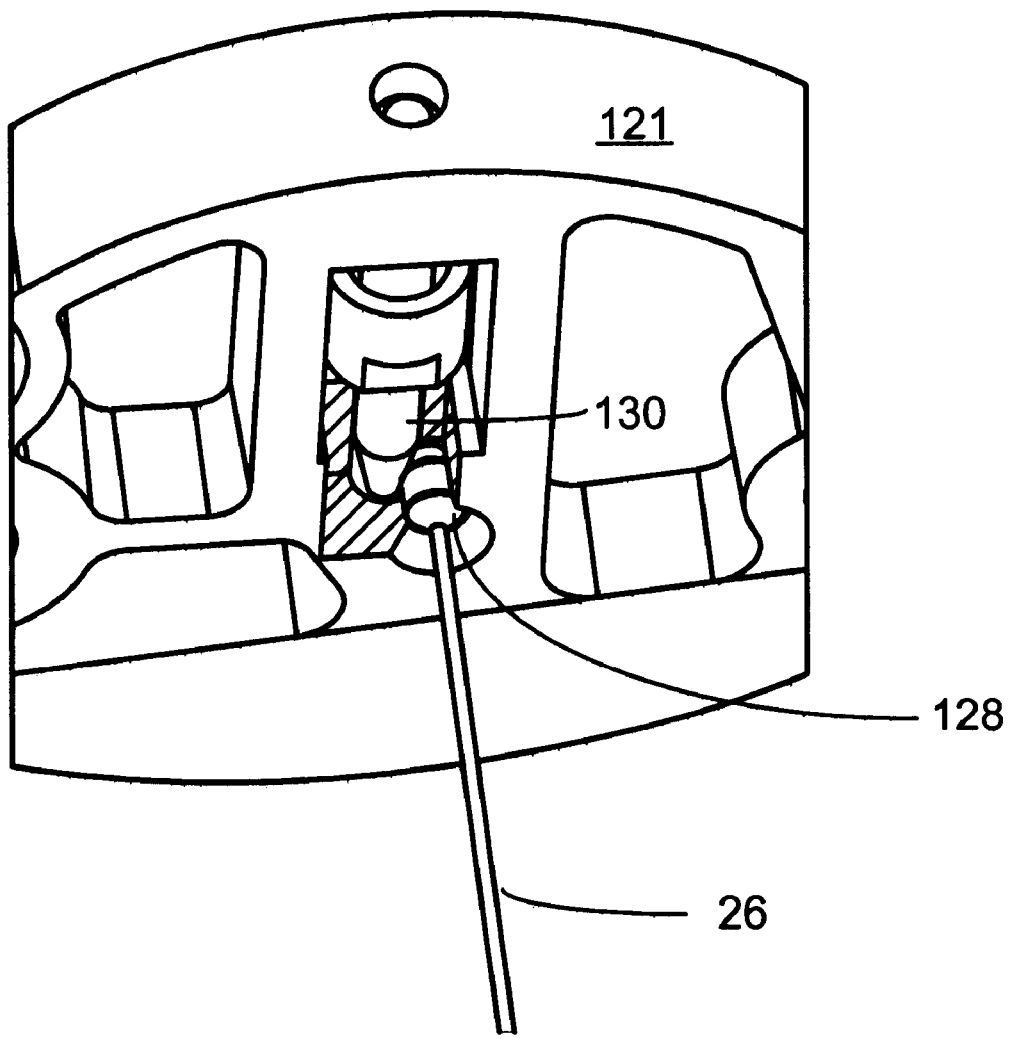
FIG. 10 is a bottom perspective view of the plunger driver of FIG. 7 (with some components removed for clarity) and plunger.

Plunger driver 32 comprises a plunger-driver base 121, a plunger-driver guide tube 123, a plunger driver volume-set rod 125, and a spring-loaded clamp 127 for holding an enlarged top end 128 of plunger 26, as shown in FIGS. 9 and 10. A plunger-drive spring 129 is coiled within guide tube 123. This spring 129 urges plunger driver base 121 toward syringe holder 30. Plunger-driver base 121 extends beyond a front wall 131 of syringe holder 30 so that it can be lifted with the thumb of a hand gripping syringe holder 30.

As shown in FIG. 10, spring-loaded clamp 127 comprises a tapered and spring-loaded pin 130 oriented slightly off the plunger axis. A "bolt" action achieves two clearly distinguishable states: "hold the plunger end" and "release the plunger end". When the plunger end is held, the spring prevents it from vibrating loose. The taper allows pin 130 to guide plunger end 128 into the desired orientation.

Volume-set rod 125, cooperates with release lever 42 (FIG. 2) to ensure that a precise and desired amount of sample is injected into injection port 14 (FIG. 1). Prior to sample extraction (and in fact prior to engagement with sample vial 36), release lever 42 (FIG. 2) is in its release orientation so that, in the absence of a user-applied counterforce, plunger-driver spring 129 urges plunger-driver base 121 against the top of syringe holder 30, which describes the pre-extraction condition of sample-injector 10. Raising plunger driver 32 manually while needle tip 38 is within sample liquid causes sample to be extracted from vial 36 and into syringe chamber 22.

Figure 11:
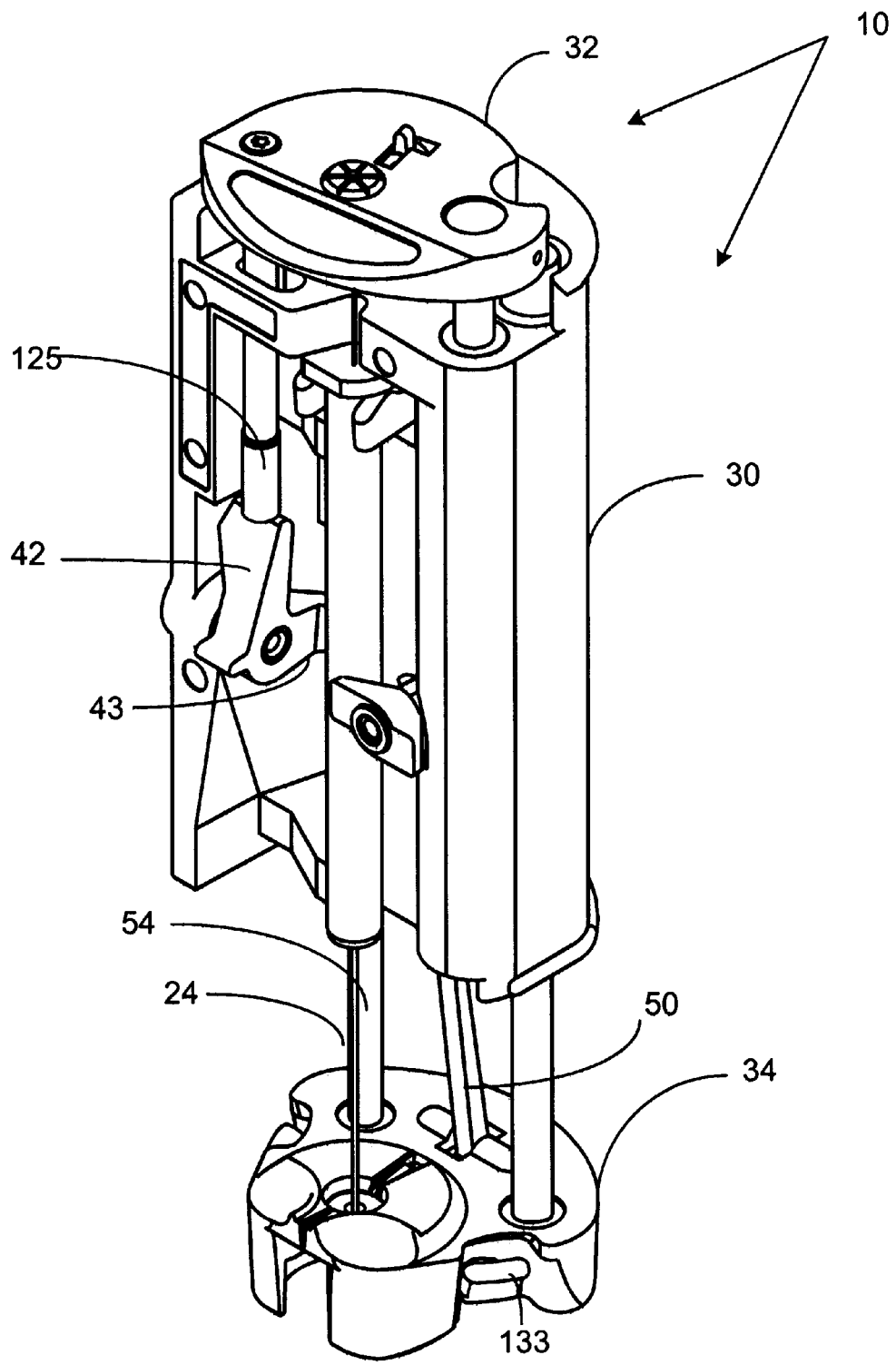
FIG. 11 is a view of the sample injector of FIG. 1 in its "ready" (fully retracted and cocked) condition.

Once sample has been extracted in excess, sample injector 10 is removed from sample vial 36. The user then manually moves release lever 42 (FIG. 11) to its cocked orientation. Excess sample is then dumped by allowing plunger-diver spring 1.29 to force plunger-driver base 121 toward syringe holder 30 until volume-set rod 125 contacts release lever 42 (which it does not contact when the latter is in its. release orientation). In its cocked orientation, release lever 42 serves as a stop so that plunger-driver base 121 cannot reach the top of syringe holder 30 (which would evacuate all sample from syringe chamber 22). Instead, syringe plunger 26 is held at an intermediate position that leaves precisely the desired quantity of sample for injection into port 14 within syringe chamber 22. At this point, sample injector 10 is in its cocked condition shown in FIG. 11. Needle 24 can be wiped at this point to remove any sample from its exterior surface.

Once the excess sample has been removed, sample injector 10 is put in its fully retracted condition. To this end, a user gently pushes interface base 52 toward syringe holder 30 by pressing on opposing tabs 133 (FIG. 5) on wings 135 of control arm 72 of interface-control lever 50. This disengages finger 115 from catch, slot 117 and forces stop arm 74 against back wall 109 of syringe holder 30. The user then diminishes the manual force to the point where interface guide-rod spring 70 can move interface 34 to its retracted position. At this point, interface-control lever resumes its safety orientation 84 and sample injector 10 assumes a "ready" condition.

Figure 12:
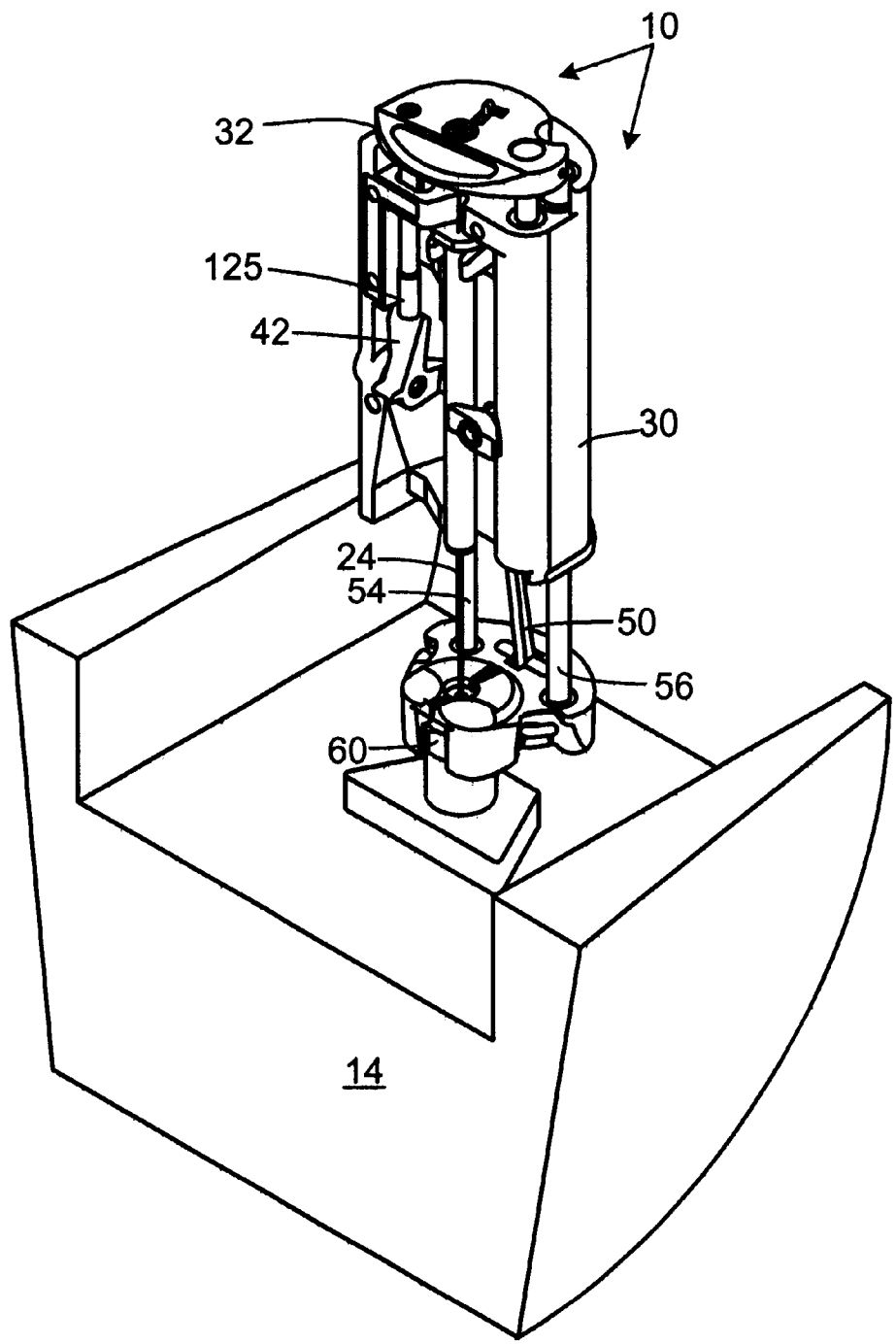
FIG. 12 is a perspective view of the sample injector of FIG. 1 in its pre-injection condition mounted on an injection port.
Figure 13:
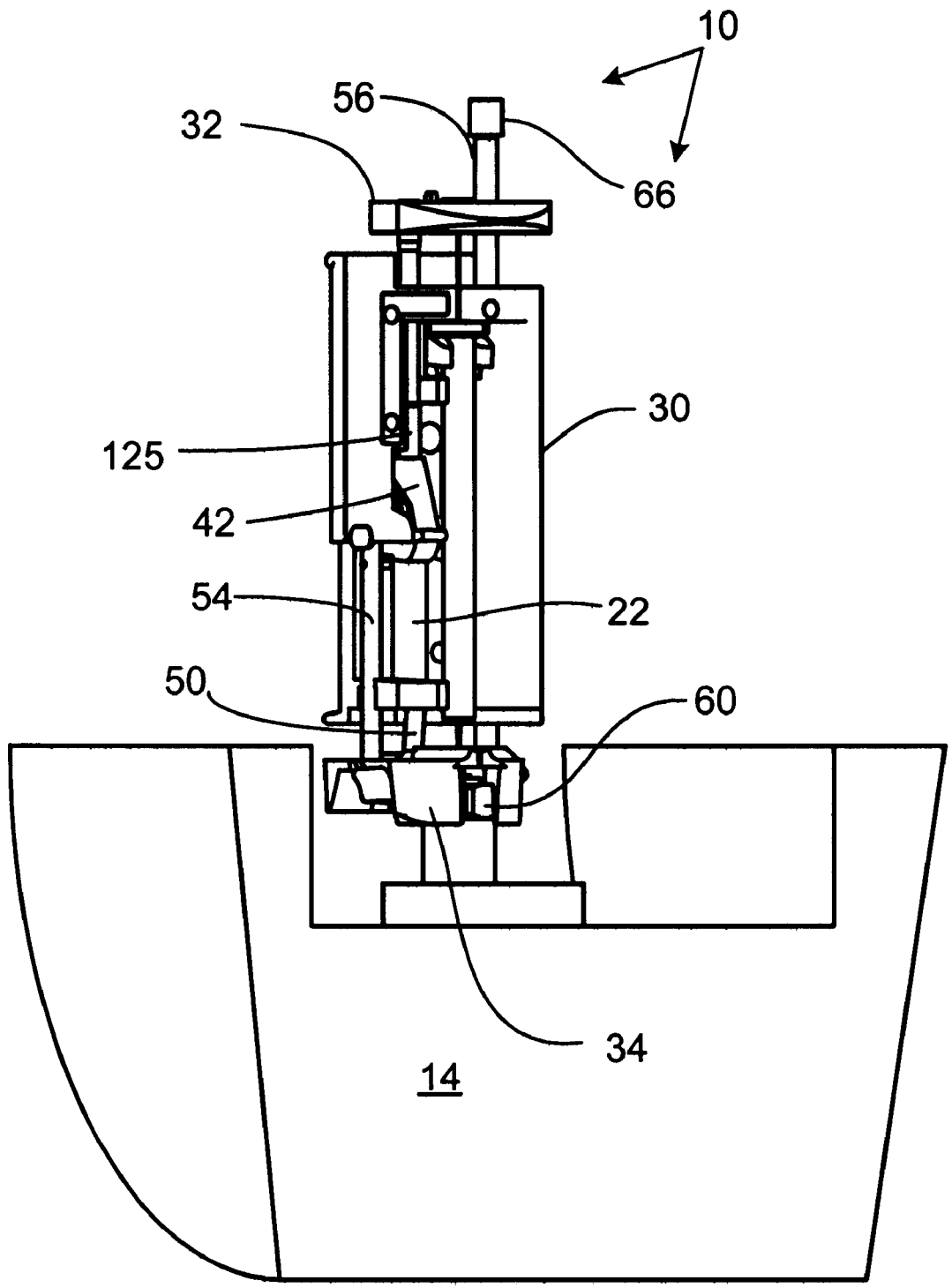
FIG. 13 is a schematic side view of the sample injector of FIG. 1 shown in a sample-release condition.

Sample injector 10, in its ready condition, is then mounted on injection port 14, as shown in FIG. 12. In the process, septum nut 60 is captured by the relatively wide mouth of injection recession 58 (FIG. 5) of interface 34 and guided by conical walls to a snug position at the base of injection recession 58. As septum nut 60 is being guided, it contacts an injection ledge 137 (FIG. 5) of control arm 72 of interface-control lever 50 and depresses it. As septum nut 60 reaches the base of injection recession 58, interface-control lever 50 assumes its injection orientation 88. At this point, sample injector 10 assumes a pre-injection condition (shown in FIG. 13).

Figure 14:
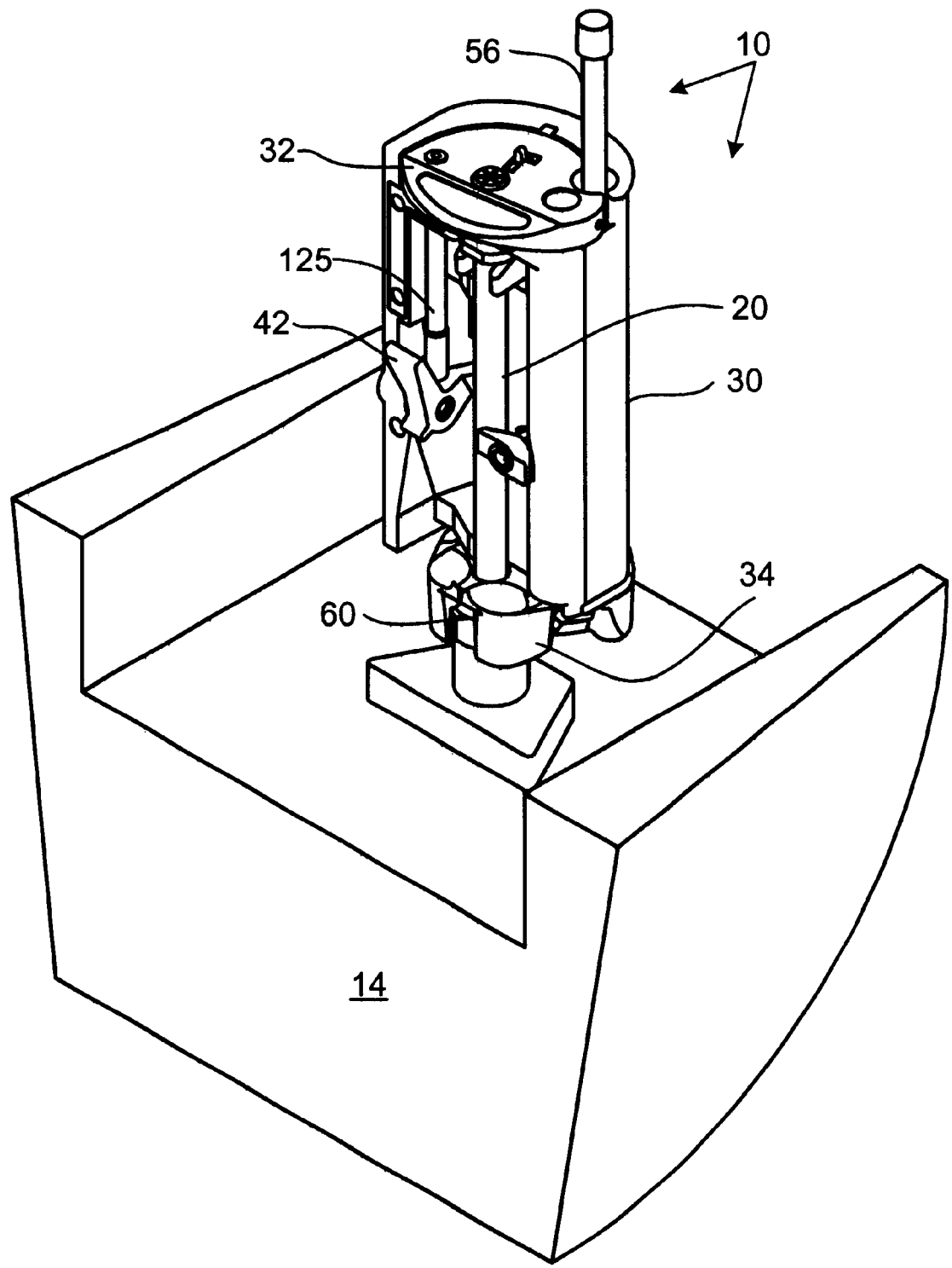
FIG. 14 is a perspective view of the sample injector of FIG. 1 in its post-injection condition just after sample injection.

With sample injector 10 in its cocked condition and interface-control lever 50 in its injection orientation 88, the relative motion of syringe holder 30 and interface 34 is again no longer constrained by safety ledge 103. Instead, a user can force syringe holder 30 down toward interface 34 as stop arm 74 is guided along a bevel 107 and then along an inner wall 108 of sample holder 30. As this happens, actuator rod 54, which is attached to interface 34, contacts an actuator arm 43 of release lever 42, forcing the latter from its cocked orientation toward its release orientation. This removes release lever 42 from the path of plunger-driver volume-set rod 125. Accordingly, plunger-driver spring 129 (FIG. 2) acts to force plunger-driver 32 toward the top 139 of syringe holder 30 so that the two contact, as shown in FIG. 14. This motion ejects the sample that was contained in syringe chamber 22 into injection port 14 at an optimal rate. As soon as the sample is injected, sample injector 10 is removed from injection port 14. This causes sample injector to assume its safety condition illustrated in FIG. 7.

The present invention provides for many alternatives to the described embodiment. Alternative arrangements can be made for adjusting the sample volume. For example, the sample adjustment assembly can be part of the syringe holder instead of the plunger driver. Likewise, there are mechanical alternatives to the disclosed release lever. These and other variations upon and modifications to the described embodiments are provided for by the present invention, the scope of which is defined by the following claims.

What is claimed is:

1. A sample injector comprising:
    a syringe holder assembly for holding a syringe body in a fixed position relative thereto;
    a plunger driver for holding a plunger of said syringe in a fixed position relative thereto, said plunger driver being movably engaged with said syringe holder so that said plunger moves relative to said syringe as said plunger driver is moved relative to said syringe holder;
    a release having a cocked position and a released position, said release in its released position allowing said plunger driver to move relative to said syringe holder so that said plunger can achieve a full ejection position relative to said syringe, said release when in its cocked position limiting movement of said plunger driver relative to said syringe holder so that said plunger is maintained at least a predetermined minimum distance from said full ejection position;
    an interface assembly for engaging a sample injection port so that sample ejected from said syringe enters said sample injection port, said interface assembly being movably engaged with said syringe holder so that said syringe can move relatively toward and away from said sample injection port, said interface assembly having an actuator that, when said release is in its cocked position and said syringe holder is moving toward said port, moves said release from its cocked position to its released position;
    a spring for providing a force opposing motion of said actuator toward said release due to motion of said syringe holder relative to said interface assembly; and
    an interface-control lever having plural selectable orientations including a injection orientation, an extraction orientation, a safety orientation, said interface-control lever when in said injection orientation allowing said actuator to move from a syringe-retracted position toward and into contact with said release, said interface-control lever when in its extraction orientation allowing said actuator to move from said syringe-retracted position toward said release but preventing it from moving into contact with said release, said interface-control lever, when in said safety orientation, preventing said actuator from moving from its needle-retracted position.

2. A sample injector as recited in claim 1 wherein said interface-control lever is pivotably connected to said interface assembly.

3. A sample injector as recited in claim 1 further comprising a catch, said interface-control lever when its extraction orientation allowing said actuator to move from said syringe-retracted position toward said release until said interface-control lever contacts said catch so that said actuator is prevented from moving into contact with said release lever.

4. A sample injector as recited in claim 3 wherein said interface-control lever and said catch have mutually engaging features that when engaged maintain said syringe holder in a relative position to said interface assembly.

5. A sample injector as recited in claim 1 further comprising an interface-control-lever spring that urges said interface-control lever toward and into said safety orientation.

6. A sample injector as recited in claim 5 wherein said interface-control lever is configured relative to said interface assembly so that when said interface assembly engages a sample vial, said vial contacts said interface-control lever so as to urge it into said extraction orientation.

7. A sample injector as recited in claim 5 wherein said interface-control lever is configured relative to said interface assembly so that when said interface assembly engages an injection port, said injection port contacts said interface-control lever so as to urge into said injection orientation.

8. A sample injector as recited in claim 1 further comprising a plunger-driver spring for urging said plunger driver in a direction that causes sample to be ejected from said syringe.

9. A sample injector as recited in claim 8 wherein, when said release is released, said plunger-driver spring urges said plunger driver to move in said direction so that sample is ejected from said syringe.

10. A sample injector comprising:
    a syringe holder assembly for holding a syringe in a fixed position relative thereto;
    a plunger driver for holding a plunger of said syringe in a fixed position relative thereto, said plunger driver being movably engaged with said syringe holder so that said plunger moves relative to said syringe as said plunger driver is moved relative to said syringe holder;

a release having a cock position and a released position, said released in its released position allowing said plunger driver to move relative to said syringe holder so that said plunger can achieve a full ejection position relative to said syringe, said released when in its cocked position limiting movement of said plunger driver relative to said syringe holder so that said plunger is maintained at least a predetermined minimum distance from said full ejection position;

an interface assembly for engaging a sample injection port so that sample ejected from said syringe enters said sample injection port, said interface assembly being movably engaged with syringe holder so that said syringe can move relatively toward and away from said sample injection port, said interface assembly having an actuator that, when said released is in its cocked position and said syringe holder is moving toward said port, moves said release from its cocked position to its released position;

a spring for providing a force opposing motion of said actuator toward said released due to motion of said syringe holder relative to said interface assembly;

an interface-control lever having plural selectable orientation including a injection orientation and an extraction orientation, said interface-control lever when in said injection orientation allowing said actuator to move from a syringe-retracted position toward and into contact with said release, said interface-control lever when in its extraction orientation allowing said actuator to move from said needle-retracted position toward said release but preventing it from moving into contact with said release; and a catch-position adjuster that when adjusted changes "a position of said syringe holder assembly relative to said interface assembly".

\* \* \* \* \*